US00PP23424P2

(12) United States Plant Patent
Donahue

(10) Patent No.: US PP23,424 P2
(45) Date of Patent: Feb. 26, 2013

(54) ***LANTANA* PLANT NAMED 'ELEMISS'**

(50) Latin Name: *Lantana camara*
Varietal Denomination: ELEMISS

(76) Inventor: Mitch Donahue, Indian Trail, NC (US)

( * ) Notice: Subject to any disclaimer, the term of this patent is extended or adjusted under 35 U.S.C. 154(b) by 37 days.

(21) Appl. No.: 13/134,479

(22) Filed: Jun. 7, 2011

(51) Int. Cl.
*A01H 5/00* (2006.01)

(52) U.S. Cl. ..... Plt./227
(58) Field of Classification Search ..... Plt./227
See application file for complete search history.

*Primary Examiner* — Susan McCormick Ewoldt
(74) *Attorney, Agent, or Firm* — Cassandra Bright

(57) ABSTRACT

A new and distinct *Lantana* cultivar named 'ELEMISS' is disclosed, characterized by a short, dense plant habit. The new variety produces yellow and pink flowers held just above the top of the canopy of the plant. Stems are more flexible than found on typical *Lantana* plants. The new variety is a *Lantana*, normally produced as an outdoor garden or container plant.

3 Drawing Sheets

Latin name of the genus and species: *Lantana camara*.
Variety denomination: 'ELEMISS'.

BACKGROUND OF THE INVENTION

The new *Lantana* cultivar is a product of a planned breeding program conducted by the inventor, Mitch Donahue, a citizen of the United States. The objective of the breeding program was to produce new *Lantana* varieties for ornamental commercial applications. The cross resulting in this new variety was made during August 2009 at a commercial nursery in Indian Trail, N.C.

The seed parent is the unpatented, proprietary seedling variety referred to as *Lantana camara* '0629' The pollen parent is the unpatented proprietary seedling variety referred to as *Lantana camara* '0643'. The new variety was discovered in Jun. 1, 2010 by the inventor in a trial field of seedlings resulting from the 2009 crossing, at the commercial nursery in Indian Trail, N.C.

Asexual reproduction of the new cultivar 'ELEMISS' by vegetative cuttings was first performed at a research greenhouse in Indian Trail, N.C. in June 2010. Subsequently, at least 5 generations have been produced, and have shown that the unique features of this cultivar are stable and reproduced true to type in successive generations.

SUMMARY OF THE INVENTION

The cultivar 'ELEMISS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ELEMISS' These characteristics in combination distinguish 'ELEMISS' as a new and distinct *Lantana* cultivar:

1. Short plant habit
2. Unique yellow and pink flower color
3. Soft, flexible stem strength, allowing plants to cover baskets attractively.

Plants of the new cultivar 'ELEMISS' are similar to plants of the seed parent, *Lantana camara* '0629' in most horticultural characteristics, however, plants of the new cultivar 'ELEMISS' are shorter and produce a different color flower. Additionally, plants of 'ELEMISS' produce soft, flexible stems not found on the seed parent.

Plants of the new cultivar 'ELEMISS' are similar to plants of the pollen parent, *Lantana camara* '0643' in most horticultural characteristics, however, plants of the new cultivar 'ELEMISS' produce larger flowers on a more upright plant form. Additionally, the new variety roots more easily than the pollen parent, and has a more vigorous growth habit.

COMMERCIAL COMPARISON

Plants of the new cultivar 'ELEMISS' are comparable to the variety *Lantana camara* 'Bright Pink', unpatented. The two *Lantana* varieties are similar in most horticultural characteristics however, the new variety 'ELEMISS' differs in having lighter, more pastel colored flowers, than the comparator variety. Additionally 'ELEMISS' produces darker foliage on shorter plants than 'Bright Pink'. Plants of 'ELEMISS' have soft stems not found on 'Bright Pink' and produces flowers closer to the upper foliage plane.

Plants of the new cultivar 'ELEMISS' are comparable to the unpatented variety *Lantana* 'Pink Caprice'. The two *Lantana* varieties are similar in most horticultural characteristics however, plants of the new variety 'ELEMISS' are much shorter and more floriferous than 'Pink Caprice'. Additionally variety 'ELEMISS' differs in having lighter, more pastel colored flowers, and shorter peduncles than 'Pink Caprice'.

BRIEF DESCRIPTION OF THE PHOTOGRAPHS

The accompanying photograph in FIG. 1 illustrates in full color a typical plant of 'ELEMISS' grown in a greenhouse, in a 1 gallon pot. Age of the plant photographed is approximately 12 weeks from a rooted cutting. As the plant illustrated in FIG. 1 has been grown in a greenhouse, the coloration is lighter than plants grown outdoors, as typical of the new variety 'ELEMISS'.

Figure 1:
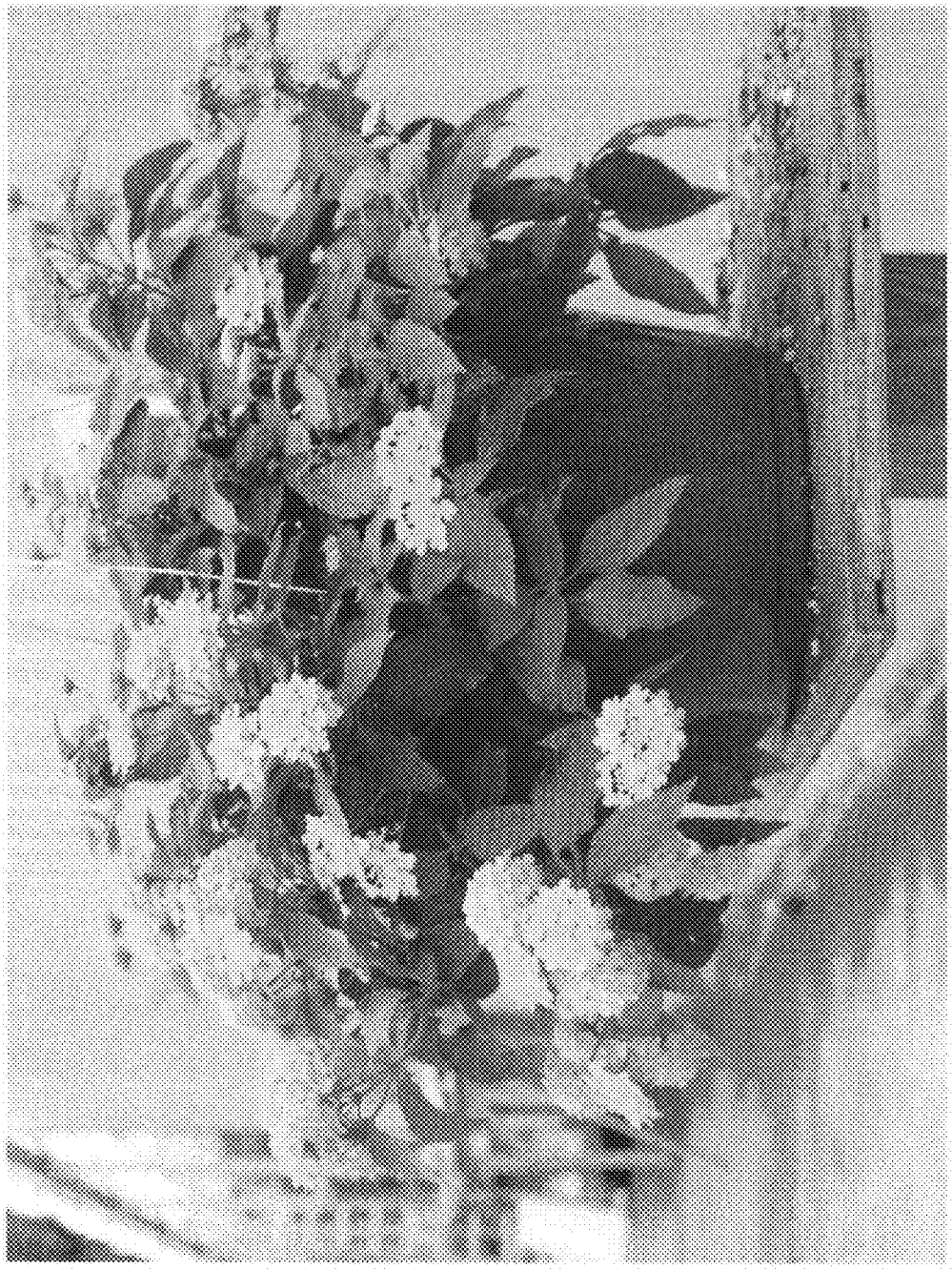
Figure 2:
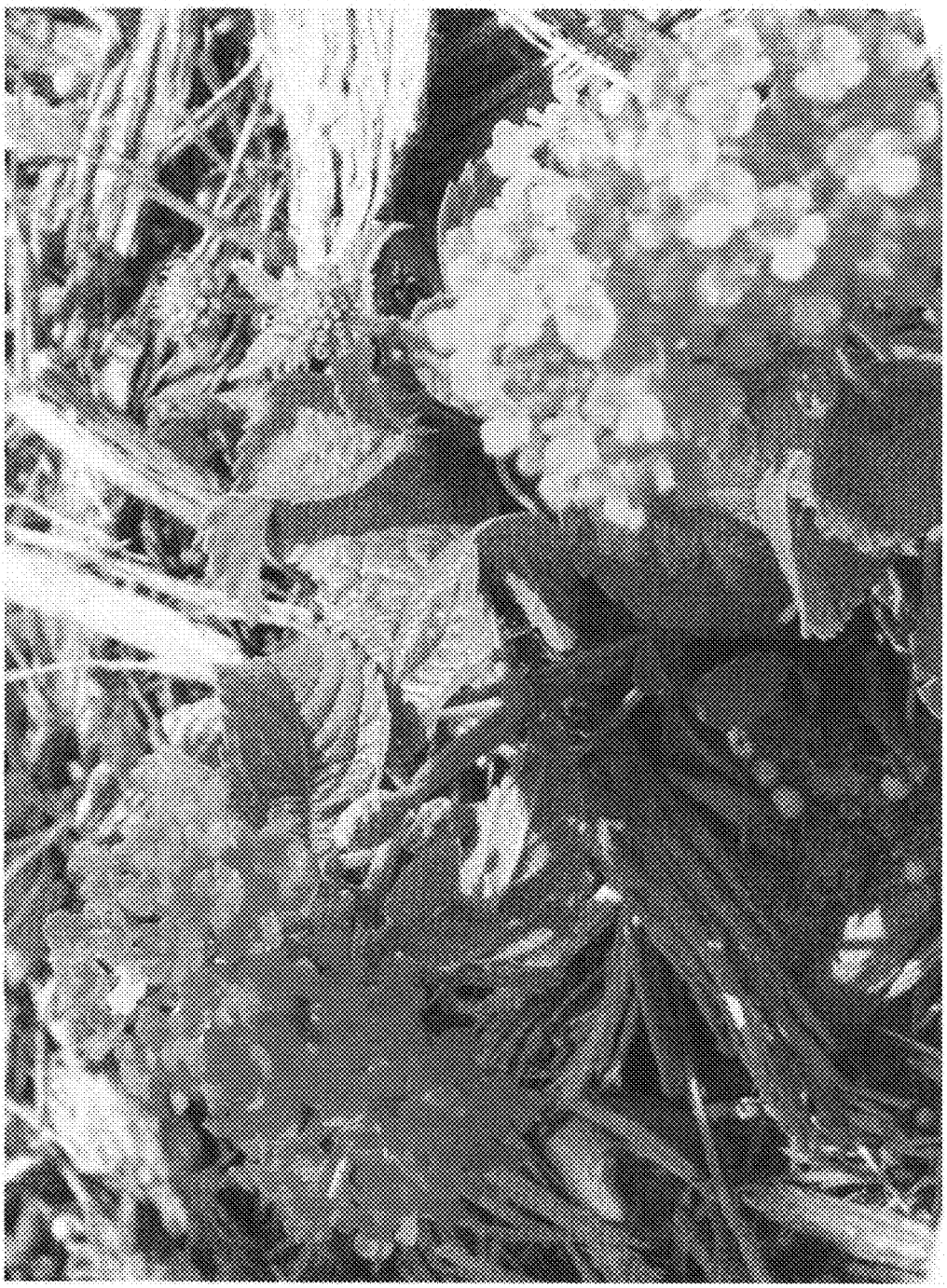
FIG. 2 illustrates in full color a close up of a typical inflorescence of 'ELEMISS', from an outdoor grown plant.
Figure 3:
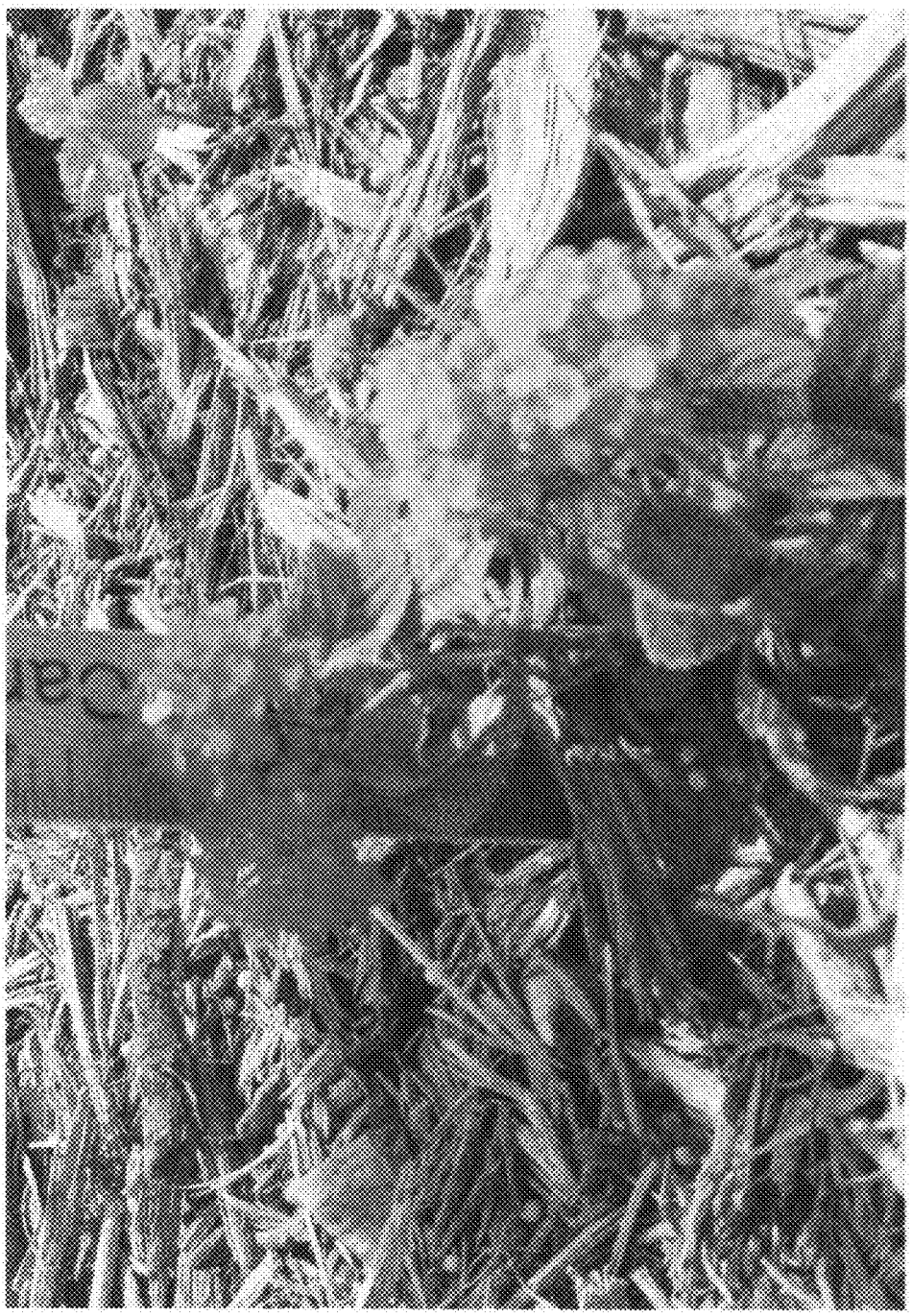
FIG. 3 is a 10 week old plant, grown outdoors in the ground in North Carolina.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ELEMISS' plants grown 10 weeks in greenhouse, then 6 weeks outdoors during spring in Indian Trail, N.C. The growing temperature ranged from 10° C. to 15° C. during the night and from 22° C. to 34° C. during the day. General light conditions are bright, normal sunlight. Measurements and numerical values represent averages of typical plant types.
Botanical classification: *Lantana camara* 'ELEMISS'.

PROPAGATION

Time to initiate roots: 10 to 14 days at approximately 15° C.
Root description: Fibrous.

PLANT

Age of plant described: Approximately 112 days from a rooted cutting.
Growth habit: Mounding to slightly trailing.
Pot size of plant described: 1 Gallon (15 cm) Pot.
Height: Approximately 20 cm.
Plant spread: Approximately 38 cm.
Growth rate: Medium vigor.
Branching characteristics: Free branching, also basal branching.
Length of primary lateral branches: Approximately 16.5 cm.
Diameter of lateral branches: 0.2 cm.
Quantity of primary lateral branches: 6 to 8.
Characteristics of primary lateral branches:
- *Form*.—Square Stem.
- *Diameter*.—0.2 cm.
- *Color*.—Near RHs Yellow-Green 144A.
- *Texture*.—Densely pubescent.
- *Strength*.—Soft, flexible.

Internode length: Average 2.5 cm.

FOLIAGE

Leaf:
- *Arrangement*.—Opposite.
- *Quantity*.—Approximately 12-14 per branch.
- *Average length*.—6.4 cm.
- *Average width*.—3.2 cm.
- *Shape of blade*.—Lanceolate.
- *Apex*.—Acute.
- *Base*.—Oblique.
- *Margin*.—Serrated.
- *Texture of top surface*.—Scabrous.
- *Texture of bottom surface*.—Smoother than upperside.
- *Pubescence*.—Densely pubescent top surface, moderately pubescent bottom surface.
- *Color*.—Young foliage upper side: Near RHS Green 143B. Young foliage under side: Near RHS Green 142B. Mature foliage upper side: Near RHS Green 137A. Mature foliage under side: Near RHS Green 137C.
- *Venation*.—Type: Pinnate. Venation color upper side: Near RHS Yellow-Green 145A. Venation color under side: Near RHS Yellow-Green 145A.
- *Petiole*.—Length: Approximately 1.1 cm. Diameter: Approximately 0.12 cm. Color: Near RHS Green 141B, underside 141C. Texture: Pubescent.
- *Other foliage characteristics*.—Leaves and petioles are less rigid than typical of *Lantana*.

FLOWER

Natural flowering season: Spring to Fall or Year Round in Warm Climate.
Days to flowering from rooted cutting: 28.
Inflorescence and flower type and habit: Corymb, 2 per node, opposite each other.
Rate of flower opening: 10 days from first color to bloom drop.
Flower longevity on plant: 6 to 8 days after opening.
Persistent or self-cleaning: Self Cleaning.
Flower fragrance: Light.
Bud:
- *Shape*.—Elongated, square at apex.
- *Length*.—0.5 cm.
- *Diameter*.—0.2 cm.
- *Color*.—Near RHS Orange-Red 32B.

Overall inflorescence size:
- *Height*.—Approximately 1.9 cm.
- *Diameter*.—Approximately 3.8 cm.
- *Flowers per inflorescence*.—30 to 35.

Individual flower size:
- *Height*.—Approximately 1.6 cm.
- *Diameter*.—Approximately 0.8 cm.
- *Corolla tube length*.—1.1 cm.
- *Corolla tube diameter*.—0.1 cm.
- *Corolla tube description*.—Pubescent a base, densely pubescent at top.

Corolla:
- *Petals/lobes*.—Number: 4, fused at base to form a corolla tube. Length: 0.4 cm — upper, 0.2 cm — lateral, 0.5 cm — lower. Width: 0.6 cm — upper, 0.2 cm — lateral, 0.3 cm — lower. Shape: Obovate. Apex: Rounded. Aspect: Slightly Rounded — Cupped. Margin: Entire, Ruffled. Texture: Glabrous. Color: Petals: Upper surface: Young flowers Near RHS Yellow 14B, transitioning to Orange 25C, mingled with Yellow-Orange 21A with age. Additional aging transitions to Red-Purple 74B, and last transition to Red-Purple 66B. Lower surface: Young flowers begin with Upper and Lower Petals near RHS Yellow 8A. Lateral petals 8A with Orange-Red 31B margin. With age, transition to Yellow 14B on fully opened blooms. Additional aging transitions to Orange 25C mingled with 21A. Next transition to Red-Purple 74B and finally Red-Purple 66B. Throat/tube: Color: Inner: near RHS White 155A. Outer: Base near Yellow-Green 144A, Mid Zone: 157B, Top Red-Purple 65C.

Calyx/sepals:
- *Form*.—5 Fused To Form Calyx.
- *Length*.—0.15 cm.

*Diameter.*—0.1 cm.
*Sepal shape*.—Tubular.
*Sepal apex*.—Acute.
*Sepal texture*.—Smooth.
*Sepal color*.—Upper surface: Near RHS Yellow-Green 145B. Lower surface: Near RHS Yellow-Green 145B.

Peduncles:
*Length*.—Approximately 3.5 cm.
*Diameter*.—Approximately 0.1 cm.
*Angle*.—Acute angle to stem.
*Strength*.—Strong.
*Texture*.—Pubescent and rough.
*Color*.—Near RHS Green 141C.

REPRODUCTIVE ORGANS

Stamens:
*Number* (*per flower*).—4.
*Filaments*.—Not present.
*Anthers*.—Shape: Oval. Length: Less than 0.1 cm. Color: Near RHS Greyed-Orange 164B.

Pollen:
*Color*.—Near RHS Yellow 13C.
*Amount*.—Sparse.

Pistils:
*Quantity per flower.*—1.
*Length.*—0.4 cm.
*Style*.—Length: 2.5 mm. Color: Near RHS Green 142D.
*Ovary color*.—Near Yellow-Green 145C.
*Stigma*.—Shape: Oval. Color: Near RHS Green 142B.

OTHER CHARACTERISTICS

Seeds and fruits: Seed Diameter: 3 mm. Color: Near RHS Brown 200A. Seed Quantity: Sparse.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'ELEMISS' as herein illustrated and described.

* * * * *